United States Patent [19]

Bendiksen et al.

[11] Patent Number: 5,087,376

[45] Date of Patent: Feb. 11, 1992

[54] MULTIFUNCTIONAL SCALE INHIBITORS

[75] Inventors: Beverly Bendiksen, Corapolis; Leonard J. Persinski; Raymond J. Schaper, both of Pittsburgh, all of Pa.

[73] Assignee: Calgon Corporation, Pittsburgh, Pa.

[21] Appl. No.: 597,652

[22] Filed: Oct. 15, 1990

[51] Int. Cl.$^5$ .............................. C02F 5/14
[52] U.S. Cl. ................................ 210/700; 210/701; 252/180
[58] Field of Search ................ 210/698–701; 252/180, 181

[56] References Cited

U.S. PATENT DOCUMENTS

| | | | |
|---|---|---|---|
| 2,961,311 | 11/1960 | Bersworth et al. | 210/698 |
| 3,288,846 | 11/1966 | Irani et al. | 252/180 |
| 4,216,163 | 8/1980 | Sommer et al. | 252/180 |
| 4,250,107 | 2/1981 | Sommer et al. | 210/700 |
| 4,640,793 | 2/1987 | Persinski et al. | 210/700 |
| 4,798,675 | 1/1989 | Lipinski et al. | 210/700 |

*Primary Examiner*—Peter Hruskoci
*Attorney, Agent, or Firm*—Raymond M. Speer; Hesna J. Pfeiffer

[57] ABSTRACT

Multifunctional scale inhibitor compositions, alone or together with polymeric structures, are described which are characterized by having, in addition to a phosphonomethylamino group, a sulfonic acid and/or carboxylic acid group. By incorporating several types of functional groups into a single molecule, control of scale formation and deposition under more severe conditions than normally encountered can be attained.

7 Claims, No Drawings

MULTIFUNCTIONAL SCALE INHIBITORS

BACKGROUND OF THE INVENTION

1. Field of the Invention

The present invention relates to compositions and methods for inhibiting the precipitation and deposition of scale-forming salts in an aqueous system.

Most industrial and commercial water contains alkaline earth metal cations, such as calcium, magnesium, etc., and several anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. These precipitates are alkaline earth metal scales. For example, when the concentrations of calcium ion and carbonate ion exceed the solubility of the calcium carbonate reaction product, a solid phase of calcium carbonate scale will form as a precipitate.

Solubility product concentrations are exceeded for various reasons, such as partial evaporation of the water phase, change in pH, pressure or temperature, and the introduction of additional ions which form insoluble compounds with the ions already present in the solution. As these reaction products precipitate on heat transfer surfaces in contact with aqueous streams, they form scale. The scale prevents effective heat transfer, interferes with fluid flow, facilitates corrosive processes, and harbors bacteria. Scale is an expensive problem in many industrial water systems, causing delays and shutdowns for cleaning and removal. Alkaline earth metal scales commonly form on the metallic surfaces of apparatuses used for thermal treatment of aqueous solutions and suspensions. By alkaline earth metal scales is meant scales including but not limited to calcium carbonate, magnesium carbonate, calcium phosphate, and calcium sulfate. These scales form frequently in the tubes of heat exchangers and on other heat exchange surfaces.

Heretofore, alkaline earth metal scale inhibition has been facilitated by the use of anionic polyelectrolytes such as polyacrylates, polymaleic anhydrides, copolymers of acrylates and sulfonates, and polymers of sulfonated styrenes. See, for example, U.S. Pat. Nos. 4,640,793; 4,650,591; and 4,671,888. However, when used as threshold alkaline earth metal scale inhibitors, large dosages of these polymers are required, which in turn increases operating costs.

Scale-forming compounds can also be prevented from precipitating by inactivating their cations with chelating or sequestering agents, so that the solubility of their reaction products is not exceeded. Generally, this requires many times as much chelating or sequestering agent as cation, since chelation is a stoichiometric reaction, and these amounts are not always desirable or economical. However, almost 50 years ago, it was discovered that certain inorganic polyphosphates would prevent such precipitation when added in amounts far less than the concentrations needed for sequestering or chelating.

When a precipitation inhibitor is present in a potentially scale-forming system at a markedly lower concentration than that required for sequestering the scale-forming cation (stoichiometric), it is said to be present in "threshold" amounts. See, for example, Hatch and Rice, *Indust. Eng. Chem.*, 31, 51-53 (1939); Reitemeier and Buehrer, *J. Phys. Chem.*, 44 (5), 535-536 (1940); Fink and Richardson U.S. Pat. No. 2,358,222; and Hatch, U.S. Pat. No. 2,539,305.

Generally, sequestering takes place at a weight ratio of threshold active compounds to scale-forming cation components of greater than about 10:1, depending on the anion components in the water. Threshold inhibition generally takes place at a weight ratio of threshold active compound to scale-forming cation components of less than about 0.5:1.0.

More recently, attention has been focused on controlling scaling under severe conditions, where conventional treatments such as those described above do not provide complete scale control. Current technology in scale control can be used to inhibit $CaCO_3$ scale up to 100 to 120 times calcite saturation, i.e., a water containing $Ca^{2+}$ and $CO_3^{2-}$ present at 100 times their solubility limit, can be prevented from precipitating as calcium carbonate scale using substoichiometric amounts of an inhibitor.

Severity of the scaling tendency of a water sample is measured using the saturation index, which may be derived in accordance with the following equation:

$$SI = \frac{(Ca^{2+})(CO_3^{2-})}{K_{spCaCO_3}}$$

where SI is the saturation index for calcium carbonate, $(Ca^{2+})$ is the concentration of free calcium ions, $(CO_3^{2-})$ is the concentration of free carbonate ions, and $K_{spCaCO_3}$ is the solubility product constant for $CaCO_3$. All of the quantities on the right side of the above equation are adjusted for pH, temperature and ionic strength.

It has been discovered that, surprisingly, when the scale inhibition compositions of the present invention are employed, in accordance with which several types of functional groups are combined into a single molecule, that scale control under these severe conditions is attainable.

One of the particular advantages of the scale inhibiting compositions of the present invention is the exceptional calcium tolerances which they exhibit. Calcium tolerance is a measure of a chemical compound's ability to remain soluble in the presence of calcium ions $(Ca^{2+})$. One of the parameters of scale control under severe conditions is pH. As pH increases, calcium tolerance decreases rapidly for traditional $CaCO_3$ threshold inhibitors, e.g., HEDP and AMP. These inhibitors precipitate with calcium at alkaline pH's, rendering them useless as threshold scale inhibitors. The addition of sulfonate groups in accordance with the present invention was intended to increase calcium tolerance. It was considered that if the sulfonated phosphonate would be soluble in the presence of $Ca^{2+}$ at high pH, it would be available to inhibit $CaCO_3$ scale. The addition of the sulfonate group has, in fact, increased the phosphonate's solubility with calcium at pH 10.2, as shown in the data further below. Performance has also been improved.

2. Brief Description of the Prior Art

The chemical compounds used in the scale inhibiting compositions of the present invention are known compounds. However, there is no teaching in the art of which applicants are aware that would in any way suggest their use in corrosion and scale inhibiting compositions in accordance with the present invention.

Sommer et al. U.S. Pat. Nos. 4,216,163 and 4,250,107 disclose N-sulfo alkane amino alkane phosphonic acids which are said to be sequestering agents useful, e.g., in decreasing the hardness of aqueous systems. While these compounds combine lower alkylene phosphonic acid groups and carboxy lower alkylene groups or alkane sulfonic acid groups in a single molecule, there is no suggestion of the particular compounds of the present invention or of their surprising effectiveness in inhibiting scale under severe conditions.

SUMMARY OF THE INVENTION

The present invention relates to a composition useful as a deposit control agent to control the formation and deposition of scale imparting compounds in an aqueous system comprising a compound of the formula:

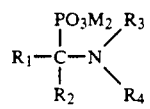

where:
- M=H, alkali metal, ammonium, or $C_{1-4}$ alkylammonium;
- $R_1$=H, $C_{1-18}$ alkyl, aryl, aryl $C_{1-4}$ alkyl, amino $C_{1-4}$ alkylene, $C_{1-4}$ alkylene phosphonic acid, $C_{1-4}$ alkylene carboxylic acid, and salts thereof;
- $R_2$=H, or phosphonic acid, and salts thereof;
- $R_3$=$C_{1-18}$ alkyl, aryl sulfonic acid, aryl $C_{1-4}$ alkyl sulfonic acid, $C_{1-4}$ alkylene sulfonic acid, $C_{1-4}$ alkylene phosphonic acid, hydroxyl, $C_{1-4}$ alkylhydroxyl, hydroxy $C_{1-4}$ alkylene sulfonic acid, and salts thereof
- $R_4$=H, $C_{1-4}$ alkylene sulfonic acid, $C_{1-4}$ alkylene phosphonic acid, $C_{1-4}$ alkylene mono- or dicarboxylic acid; and $C_{1-4}$ alkylene substituted by one carboxylic acid or $C_{1-4}$ alkylene carboxylic acid and one sulfonic acid or $C_{1-4}$ alkylene carboxylic acid; and salts of all of the above.

The present invention further relates to a method of inhibiting the precipitation and deposition of scale-forming salts in an aqueous system, comprising the step of adding to said system an amount sufficient to establish a concentration of from 1 to 150 mg/L of a compound of formula (I).

The present invention also relates to a method of inhibiting the precipitation and deposition of scale-forming salts in an aqueous system, comprising the step of adding to said system an amount sufficient to establish a concentration of from 1 to 150 mg/L of a compound of formula (I), together with a member selected from the group consisting of: homo- and copolymers comprising one or more of acrylamide, acrylic acid, 2-acrylamido-2-methyl propane sulfonic acid, methacrylic acid, itaconic acid, polyethylene glycol monomethacrylate, maleic anhydride, maleic acid, t-butyl acrylamide, sodium styrene sulfonate, sodium vinyl sulfonate, hydroxy propyl acrylate, hydroxy propyl methacrylate, 3-allyloxy-2-hydroxy propane sulfonic acid, sodium salt, and vinyl phosphonic acid. Molecular weights for such polymer additives should range from 500 to 250,000 amu. For example, such compositions may range from copolymers of 90/10 to 10/90 AA/AMPS, with the most preferred composition being from 30/70 to 70/30 AA/AMPS.

DETAILED DESCRIPTION OF THE INVENTION

The scale inhibiting compositions of the present invention employ one of the species represented by Formula I above. In particular, three species are preferred and are set out below:

$(H_2PO_3CH_2)_2NCH_2COOH$ $(H_2PO_3CH_2)_2NCH_2CH_2SO_3H$

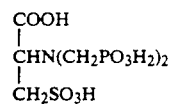

When any of the above compounds is used to inhibit the precipitation and deposition of scale-forming salts in an aqueous system, it can be effectively employed for that purpose when added in amounts sufficient to establish a concentration in said aqueous system of from 1 to 150 mg/L. Preferably, the amount added will be sufficient to establish a concentration of from 10 to 100 mg/L, and most preferably, the amount added will be sufficient to establish a concentration of from 20 to 75 mg/L of the compound.

The phrase "inhibiting the precipitation" is meant to include threshold inhibition, dispersion, solubilization, or particle size reduction.

The phrase "scale-forming salts" is meant to include any of the scale-forming salts, including, but not limited to, calcium carbonate, calcium sulfate, calcium phosphate, calcium phosphonate (including calcium hydroxyethylidene diphosphonic acid), calcium oxalate, calcium fluoride, barium sulfate and magnesium salts.

The phrase "aqueous system" is meant to include any commercial or industrial system containing or utilizing water, including, but not limited to, cooling water, boiler water, desalination, gas scrubbers, blast furnaces, sewage sludge, thermal conditioning equipment, reverse osmosis, sugar evaporators, paper and pulp processing, mining circuits, and the like.

The compounds employed in the scale inhibiting compositions of the present invention may be made in a straightforward manner using any of the methods of preparation readily available to, and within the knowledge and experience, of a person of ordinary skill in the synthesis of organic compounds. For example, it is possible to utilize the Mannich Reaction of amine, formaldehyde and phosphorus acid, in a manner analogous to that described in U.S. Pat. No. 3,288,846, to prepare the compounds of the present invention. A further description of this type of synthesis may be found in Moedritzer and Irani, "The Direct Synthesis of α-Aminomethylphosphonic Acids, Mannich-Type Reactions with Orthophophorous Acid", *J. Org. Chem.*, 31, 1603-7 (1966).

Preparation of two of the compounds utilized in the compositions and methods of the present invention, following such a proposed synthesis, is shown in the following schematic diagrams:

$H_2NCH_2CH_2SO_3H$ + 2HCHO + $2H_3PO_3 \longrightarrow$
(Taurine)

$(H_2PO_3CH_2)_2NCH_2CH_2SO_3H$

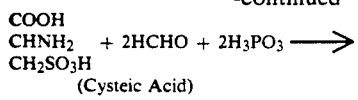
(Cysteic Acid)

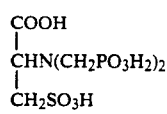

In the preferred embodiments of the present invention, it is contemplated that only a single compound of those described above would be used for the purpose of inhibiting scale. However, it is also contemplated that one of these compounds could be combined with one or more polyelectrolytes of the type described above so as to provide an even more effective product for the inhibition of scale.

For example, there could be used in such a combination homo- and copolymers comprising one or more monomers of acrylamide, acrylic acid, 2-acrylamido-2-methyl propane sulfonic acid, methacrylic acid, itaconic acid, polyethylene glycol monomethacrylate, maleic anhydride, maleic acid, t-butyl acrylamide, sodium styrene sulfonate, sodium vinyl sulfonate, hydroxy propyl acrylate, hydroxy propyl methacrylate, 3-allyloxy-2-hydroxy propane sulfonic acid, sodium salt, and vinyl phosphonic acid. Molecular weights for such polymer additives should range from 500 to 250,000 amu. For example, such compositions may range from copolymers of 90/10 to 10/90 AA/AMPS, with the most preferred composition being from 30/70 to 70/30 AA/AMPS. Combinations using these polymers together with the compositions of the present invention can increase the amount of scale control and deposit control which is achieved.

EXAMPLES OF PREFERRED EMBODIMENTS

The following examples are presented for the purpose of illustrating the present invention, but are not intended to be in any way a limitation thereof.

EXAMPLE 1

N,N-bis(phosphonomethyl)taurine

To a 500 ml 3-neck flask fitted with a magnetic stirrer, thermometer, condenser and addition funnel is added 62.58 g (0.50 moles) of taurine, 64.21 g water, 82.00 g (1.0 moles) of phosphorus acid and 50 ml of concentrated hydrochloric acid. This mix is heated to reflux and 150 g (1.85 moles) of 37% formaldehyde is added over a 35 minute period.

After the addition, the volume of the flask is reduced by ¼ and the entire reaction mixture is concentrated on a rotary evaporator at full vacuum with heat to yield an off-white solid. The solid is taken up in water to provide an aqueous solution of 52.1%. Based on carbon-13, phosphorus-31 and proton NMR, conversion to the desired structure was approximately 97%.

EXAMPLE 2

N,N-bis(phosphonomethyl)glycine

To a 500 ml 3-neck flask fitted with a magnetic stirrer, thermometer, condenser and addition funnel is added 37.5 g (0.50 moles) glycine, 38.27 g water, 82.00 g (1 mole) of phosphorus acid and 50 ml of concentrated hydrochloric acid.

The mix is heated to reflux and 150 g (1.85 moles) of 37% formaldehyde is added over a 40 min period. The product was worked up as in Example 1 above to yield a solid product. Based on carbon-13, phosphorus-31 and proton NMR, conversion to the desired structure was approximately 98%.

EXAMPLE 3

N,N-bis(phosphonomethyl)cysteic acid

To a 250 ml 3-neck flask fitted with a magnetic stirrer, thermometer, condenser and addition funnel is added 46.80 g (0.25 moles) of cysteic acid, 46.80 g water, 41.0 g (0.50 moles) phosphorus acid, and 25 ml of concentrated hydrochloric acid. The mix is heated to reflux and 75 g (0.925 moles) of 37% formaldehyde is added over a 40 min period.

The product is worked up in the same manner as in Example 1 above to yield an aqueous solution of 46.58%. Based on NMR analysis, conversion to the desired structure was 56%.

EXAMPLE 4

Standard Test Conditions

The compound of Example 1 was evaluated for $CaCO_3$ scale inhibition at pH 8 and 56X $CaCO_3$ S. I. in accordance with following test protocol:

Conditions: 200 mg/L $Ca^{2+}$; 600 mg/L total alkalinity as $HCO_3^-$; pH obtained from natural buffering of an $HCO_3^-$; 60° C. for 24 hrs.

Procedures: (1) acid wash and rinse flasks and stoppers; (2) place distilled water in flask; (3) add inhibitor at desired concentration; (4) add 25 ml of 0.10M $CaCl_2 \cdot 2H_2O$ solution to provide 200 mg/L $Ca^{2+}$; (5) place flask on pH meter with mixing; (6) add 4.9 ml of 1M $NaHCO_3$ to give 600 mg/L $HCO_3$ (total volume 500 ml); (7) record pH of approximately 8 and place stoppered flask in a beaker bath or oven at 60° C.; (8) at 24 hrs, remove flask and filter 100 ml aliquot through Whatman 42 filter paper; and (9) titrate filtrate for calcium content by the Schwarzenbach method; calculate percent inhibition.

The results of these evaluations are shown in the table of data below.

TABLE I

| | % Inhibition | |
|---|---|---|
| Dose (mg/L) | HEDP | Compound of Ex. 1 |
| 0.05 | 57 | 0 |
| 0.10 | 53 | 11 |
| 0.15 | 32 | 47 |
| 0.20 | 100 | 76 |
| 0.25 | 99 | 47 |
| 0.30 | 100 | 2 |
| 0.35 | 100 | 42 |
| 0.40 | 100 | 43 |
| 0.45 | 100 | 66 |
| 0.50 | 100 | 78 |

HEDP = Hydroxyethylidene diphosphonic acid, a commercial scale control agent.

The compound of Example 1 did not give performance comparable to a currently used treatment (HEDP) under these standard conditions.

EXAMPLE 5

Severe Test Conditions

AMP, a commercial product, and the compounds of Examples 1-3 were evaluated for $CaCO_3$ scale inhibition at pH 9 in accordance with following test protocol:

Conditions: 250 mg/L $Ca^{2+}$; 600 mg/L total alkalinity as $HCO_3^-$; pH obtained from natural buffering of an 80% $HCO_3^-$/20% $CO_3^{2-}$ mixture; 55° C. for 24 hrs.

Procedures: (1) acid was and rinse flasks and stoppers; (2) place distilled water in flask; (3) add inhibitor at desired concentration; (4) add 10 ml of 0.313M $CaCl_2\cdot 2H_2O$ solution to provide 250 mg/L $Ca^{2+}$; (5) place flask on pH meter with mixing; (6) add 10 ml of 33 g/L of $NaHCO_3$ to give 480 mg/L $HCO_3^-$ and 10 ml of 10.6 g/L $Na_2CO_3$ to give 120 mg/L $CO_3^{2-}$; (7) record pH of approximately 9 and place stoppered flask in a beaker bath or oven at 55° C.; (8) at 24 hrs, remove flask and filter 100 ml aliquot through Whatman 42 filter paper; and (9) titrate filtrate for calcium content by the Schwarzenbach method; calculate percent inhibition.

The results of these evaluations are illustrated in the table of values below.

TABLE II

| Test Sample No. | Composition | % Inhibtion at mg/l | | | | | Calcium Tolerance |
|---|---|---|---|---|---|---|---|
| | | 10 | 20 | 30 | 40 | 50 | |
| Ex. 2 | $(H_2PO_3CH_2)_2NCH_2COOH$ | 76 | 84 | 79 | 84 | 77 | 280 |
| Ex. 1 | $(H_2PO_3CH_2)_2NCH_2CH_2SO_3H$ | 88 | 86 | 90 | 92 | 84 | 1360 |
| Ex. 3 | COOH<br>\|<br>$CHN(CH_2PO_3H_2)_2$<br>\|<br>$CH_2SO_3H$ | 76 | 74 | 82 | 87 | 83 | 490 |
| AMP | $N(CH_2PO_3H_2)_3$ | 7 | 21 | 22 | 30 | 30 | <1 |

Calcium Tolerance = mg phosphonate/10,000 mg Ca/liter

The results of these evaluations showed that these compounds were capable of 75 to 92% inhibition at dosages between 10 and 50 ppm, while an acceptable commercial product, AMP, was far inferior.

EXAMPLE 6

Further experiments were run investigating the effect of pH of the aqueous system under test conditions of 300 times $CaCO_3$ saturation, i.e., the test conditions of Example 5. Results are shown in Table III below.

TABLE III

| % $CaCO_3$ Inhibition at 300X Saturation $CaCO_3$ | | | | | |
|---|---|---|---|---|---|
| Sample | Dosage (ppm) | pH:8 | 8.5 | 9 | 9.5 |
| Commercial Product (pHreeGUARD 2300) | 25 | 73.1 | 56.0 | 75.5 | 22.6 |
| | 50 | 81.9 | 48.3 | 74.0 | 38.2 |
| | 75 | 94.0 | 64.6 | 78.2 | 47.6 |
| Compound of Example 1 + TRC-233 (1/1.5) | 25 | 38.6 | 47.1 | 99.3 | 30.0 |
| | 50 | 100.8 | 97.1 | 96.9 | 91.5 |
| | 75 | 97.6 | 97.1 | 98.1 | 99.8 |

TRC233 = AA/AMPS (60/40)

From this data, unexpectedly good results were obtained over a broad range of conditions, indicating that this particular embodiment of the present invention allows one to operate effectively at severe scaling conditions.

EXAMPLE 7

The compounds of Example 1 was evaluated for $CaCO_3$ scale inhibition in combination with various polymers. The test protocol was that of Example 5, the severe conditions test. The results obtained are illustrated below in Table IV.

TABLE IV

| N, N-bis(phosphonomethyl) taurine/Polymer Mixtures % Inhibition at Dosage Level | | | | | |
|---|---|---|---|---|---|
| Sample | 10 mg/L | 20 mg/L | 30 mg/L | 40 mg/L | 50 mg/L |
| Control: pHGD2300 (HEDP/AMP/TRC-233) | 66 | 61 | 70 | 77 | 78 |
| Example 1: | | | | | |
| + TRC-233 | 55 | 95 | 100 | 94 | 94 |
| + WTP-1 | 52 | 64 | 88 | 90 | 99 |
| + 315A | 82 | 92 | 87 | 82 | 82 |
| + 2921-80C | 70 | 85 | 85 | 91 | 95 |
| + JW-1 | 57 | | 90 | | 95 |

JW-1 = 1/1/1 TRC-233/315A/WTP-1
TRC-233 = 60/40 AA/AMPS
WTP-1 = Rohm & Haas carboxylate terpolymer
315A = carboxylate terpolymer
2921-80C = 60/20/20 AA/AMPS/VPA
AA = acrylic acid
AMPS = 2-acrylamido-2-methyl-propanesulfonic acid
VPA = vinylphosphonic acid In all of the above combinations, the ratio of the Example 1 compound to Polymer = 1.5/1

The above results show the improvement over a commercial product control obtained with a variety of polymeric combinations, over a broad compositional range at various dosing rates.

EXAMPLE 8

Scale Adherence Test

The compounds prepared in Examples 1-3 were tested for their ability to control scale adherence on heat transfer surfaces in combination with polymers.

Equipment

Apparatus loop includes a hot bath, a cold bath and 3 cells. Each cell consists of a jacketed beaker equipped with heat transfer "U" tube (Admiralty Brass), pH controller, level controller, thermometer, air vents and make-up tank. The total volume was 950 ml.

Procedures

1. Tubes precleaned with 50:50 $HCl:H_2O$ for 25 sec. Rinsed copiously with deionized $H_2O$ and scoured with a nylon pad.

2. Water baths for the jacketed beaker an U tube set to maintain temperature of bulk water at 50°-55° C.

3. Position "U" tubes in lids so that the same amount of tubing is exposed in each cell.

4. Add enough preheated $H_2O$ to cover pH electrode bulb; add desired amount of inhibitor solution; add 120 mg/L of $Ca^{2+}$. Adjust pH to 7.5±0.1 using 1.0N NaOH.

5. Mix volume alkalinity solution to give 180 mg/L $HCO_3$ with the remaining preheated $H_2O$ and immediately add to the cell. pH should rise to 9.0±0.1.

6. Air flow is adjusted to give an evaporation rate of ⅜ L/day.

7. Makeup tank contains stable solution of 60 mg/L $Ca^{2+}$ and 90 mg/L $HCO_3$ which is added on demand as the water in the jacketed beaker evaporates. This concentrates and supersaturates the $Ca^{2+}:CO_3^{2-}$. The test is run for five to six days to concentrate the solution until 325 mg/L $Ca^{2+}$ and 486 mg/l $HCO_3^-$ are present, pH 9, 55° C. to give approximately 300 times $CaCO_3$ saturation.

8. Once the appropriate supersaturation is attained, the makeup tank is switched to deionized water and the tests are continued for 24 hours. Total test time is 6 days.

Deposit Analyses

Rinse any deposit or coating from tube with 1:3 $HCl:H_2O$ into same beaker. Also wash tube well with distilled $H_2O$ into same beaker. Neutralize washing to pH 4-7 with conc. NaOH solution. Transfer to 250 ml volumetric; dilute to mark. Analyze 25 ml aliquots for Ca by titrating with 0.01M EDTA solution. Report as mg Ca tube deposit.

Using the procedure described above, the deposit weights obtained were as illustrated in Table V below.

TABLE V

| Scale Adherence Test | |
|---|---|
| Sample (dose 25 mg/L active) | Deposit Wt/MgCa |
| Blank | 124.0 |
| pHreeGuard ® | 16.1 |
| Ex. 1/TRC-233 1.5/1 | 1.12 |
| Ex. 1/315A 1.5/1 | 1.84 |
| Ex. 1/JW-1 1.5/1 | 1.32 |
| Ex. 1/TRC-271 1.5/1 | 1.76 |
| Ex. 2/315A | 10.52 |
| Ex. 3/315A | 2.36 |

TRC-271 = AA/AMPS/HEM-5
HEM-5 = polyethylene glycol monomethacrylate

The above test results indicate great improvement over the blank and substantial improvement in activity compared to a commercial treatment, pHreeGUARD 2300.

EXAMPLE 9

Further testing of the ability of the composition of the present invention to prevent deposits was performed in a pilot cooling tower. The system is a recirculating cooling tower with four single tube exchangers connected in series. There are two banks of heat exchangers side by side with ¾" stainless steel and ½" admiralty brass tubes. The flow rate through the system was 3.0 gpm with an inlet temperature of 110° F. and an outlet temperature of 133° F., =ΔT 23° F. Treatments used were 25 mg/L active: 2/1/2 AMP/HEDP/TRC-233 in Side A; 25 mg/L active: 1.5/1 Example 1/TRC-233 in Side B. The same makeup water as used in Example 8 was used in the test. The systems were cycled up to 5.4 cycles of concentration giving a target of 300 times $CaCO_3$ saturation. The systems were held at the target saturation by controlling the conductivity of the water for 24 days, after which time the heat transfer tubes were pulled and deposit weights for the two treatments determined. Results were as follows:

TABLE VI

| Deposit on Stainless Steel Tubes | | |
|---|---|---|
| Treatment A | AMP/HEDP/TRC-233 | 4.2406 g |
| Treatment B | Ex. #1/TRC-233 | 0.0145 g |

The scale inhibitor of the present invention reduced the deposit compared to conventional treatment by a factor of 300.

What is claimed is:

1. A method of inhibiting the precipitation and deposition of scale-forming salts including calcium carbonate in an aqueous system having a pH of at least about 9, comprising the step of adding to said system an amount sufficient to establish a concentration of from 1 to 150 mg/L of a compound selected from N,N-bis(phosphonomethyl)taurine of the formula $(H_2PO_3CH_2)_2NCH_2CH_2SO_3H$ and N,N-bis(phosphonomethyl)cysteic acid of the formula

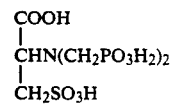

2. A method according to claim 1 wherein the compound is $(H_2PO_3CH_2)_2NCH_2CH_2SO_3H$.

3. A method according to claim 1 wherein the compound is

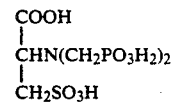

4. A method according to claim 1 wherein the amount of compound added is sufficient to establish a concentration of from 10 to 100 mg/L.

5. A method according to claim 1 wherein the amount of compound added is sufficient to establish a concentration of from 20 to 75 mg/L.

6. A method of inhibiting the precipitation and deposition of scale-forming salts including calcium carbonate in an aqueous system having a pH of at least about 9, comprising the step of adding to said system an amount sufficient to establish a concentration of from 1 to 150 mg/L of a compound selected from N,N-bis(phosphonomethyl)taurine of the formula $(H_2PO_3CH_2)_2NCH_2CH_2SO_3H$ and N,N-bis(phosphonomethyl)cysteic acid of the formula

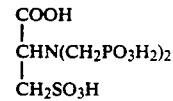

together with one or more members selected from the group consisting of homo- and co-polymers comprising one or more monomers of acrylamide, acrylic acid, 2-acrylamido-2-methyl propane sulfonic acid, methacrylic acid, itaconic acid, polyethylene glycol monomethacrylate, maleic anhydride, maleic acid, t-butyl acrylamide, sodium styrene sulfonate, sodium vinyl sulfonate, hydroxy propyl acrylate, hydroxy propyl methacrylate, 3-allyloxy-2-hydroxy propane sulfonic acid, sodium salt, and vinyl phosphonic acid.

7. A method according to claim 6 wherein the molecular weight of the polymer employed in the combination therein ranges from 500 to 250,000 amu.

* * * * *